United States Patent [19]

Deneke et al.

[11] Patent Number: 4,591,553

[45] Date of Patent: May 27, 1986

[54] PROCESS AND ANALYTICAL AGENT FOR THE DETERMINATION OF THE ACTIVITY OF GLUTAMATE-OXALACETATE-TRANSAMINASE

[75] Inventors: Ulfert Deneke, Mörlenbach; Wolfgang Gruber, Tutzing-Unterzeismering; Hans-Georg Batz, Tutzing, all of Fed. Rep. of Germany

[73] Assignee: Boehringer Mannheim GmbH, Mannheim, Fed. Rep. of Germany

[21] Appl. No.: 500,111

[22] Filed: Jun. 1, 1983

[30] Foreign Application Priority Data

Jun. 9, 1982 [DE] Fed. Rep. of Germany ....... 3221730

[51] Int. Cl.$^4$ ................................................ C12Q 1/52
[52] U.S. Cl. ........................................ 435/16; 435/25; 435/28; 435/805
[58] Field of Search .................. 435/16, 28, 25, 805

[56] References Cited

U.S. PATENT DOCUMENTS

| | | | |
|---|---|---|---|
| 3,701,601 | 10/1972 | Plumpe et al. | 435/16 |
| 3,875,014 | 4/1975 | Forgione . | |
| 4,089,747 | 5/1978 | Bruschi | 435/805 |
| 4,184,923 | 12/1980 | Schubert | 435/10 |

FOREIGN PATENT DOCUMENTS

2911481 10/1979 Fed. Rep. of Germany .
3026854 11/1980 Fed. Rep. of Germany .

OTHER PUBLICATIONS

Anonymous, 1977 Research Disclosure, vol. 160, Item No. 16034, pp. 19–24.
Narahara et al., Chemical Abstracts, vol. 93, 1980, Item No. 217039z.
Watanabe et al., Chemical Abstracts, 1982, vol. 96, Item No. 195584f.
Abstracts of Scientific Sessions (Clin. Chemistry) vol. 6, No. 4, 1960.
Transaminase Activity in Human Blood, Jour. Clin. Invest. vol. 34, 1955.
Determination of Transaminase, Ame. Jor. Clin. Path. vol. 28, 1957.
Clin. Chim, Acta 28(1970) 431–437.
Bioquimica Clic. Vo. 2 No. 5, 25–36 (1971) Nuevo Metodo Colorimetrico para la Determinacion de Algunas Enzimas. Part 1.
Die Bedeutung der Enzymatischen Analyse in der Medizin.

*Primary Examiner*—Sam Rosen
*Assistant Examiner*—William J. Herald
*Attorney, Agent, or Firm*—Felfe & Lynch

[57] ABSTRACT

The present invention provides a process for the determination of the activity of glutamateoxalacetate-transaminase (GOT) in aqueous solutions in which (a) α-ketoglutarate is reacted with alanine-sulphinic acid, catalyzed by GOT, to give pyruvate, sulphur dioxide and glutamate, (b) the resultant pyruvate is reacted with phosphate and oxygen, catalyzed by pyruvate oxidase, to give acetyl phosphate, carbon dioxide and hydrogen peroxide, (c) the hydrogen peroxide and a chromogen is reacted, catalyzed by a peroxidase, to give a dyestuff and water and (d) the amount of dyestuff formed is determined, wherein the chromogen used is N-(3'-sulphonyl-4'-hydroxy-5'-chlorophenyl)-4-aminoantipyrine (SHYC-AA), 4,5-bis-[4-dimethylaminophenyl]-2-[3,5-dimethoxy-4-hydroxyphenyl]-imidazole (B-DDH-imidazole) or a related substance.

The present invention also provides an analytical agent for the determination of the activity of GOT, comprising α-ketoglutarate, alanine-sulphinic acid, a chromogen, peroxidase, pyruvate oxidase, soluble phosphate, buffer and water, wherein the chromogen is N-(3'-sulphonyl-4'-hydroxy-5'-chlorophenyl)-4-aminoantipyrine (SHYC-AA) or 4,5-bis-[4-dimethylaminophenyl]-2-[3,5-dimethoxy-4-hydroxyphenyl]-imidazole (B-DDH-imidazole).

12 Claims, 1 Drawing Figure

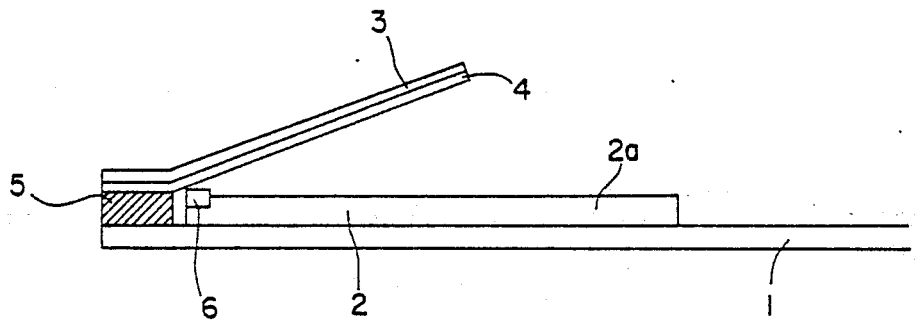

PROCESS AND ANALYTICAL AGENT FOR THE DETERMINATION OF THE ACTIVITY OF GLUTAMATE-OXALACETATE-TRANSAMINASE

The present invention is concerned with a process and an analytical agent for the determination of the enzyme glutamate-oxalacetate-transaminase (GOT), which process can be carried out on a reagent carrier, such as a test strip. The process can be used for the determination of GOT in biological fluids, such as serum or urine, or in other materials.

The determination of GOT in plasma, serum, tissues and other biological materials is of great importance for the diagnosis and differential diagnosis of, for example, liver, heart and muscle diseases. (For the importance of these determinations see, for example, H. U. Bergmeyer, Methoden der enzynamtischen Analyse, 3rd edition, 1974, pub. Verlag Chemie Weinheim, Volume I, pages 6–74). Therefore, various processes have already been described for the determination of GOT, all of which, however, have disadvantages (see Bergmeyer, loc. cit., pp. 769–799).

GOT catalyses the following reactions:

(1a)

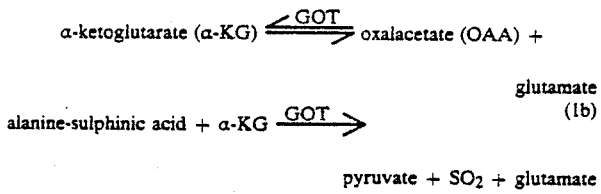

(1b)

For the determination of the activity of this enzyme, various processes are known which measure either the decrease of one of the starting materials or the rate with which one of the end products of the reaction equations (1a) or (1b) is formed.

Thus, A. Karmen (J. Clin. Invest., 34, 133–135/1955) describes a test in which the OAA formed in equation (1a) is measured as follows:

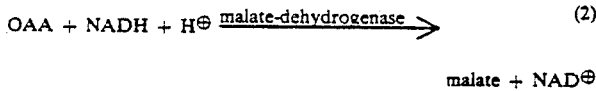

(2)

The decrease of the absorption of NADH per minute, measured at 365 nm., is the measurement signal.

Another process for the detection of GOT has been described by S. Reitmann and S. Frankel (Am. J. Clin. path., 28, 56–63/1957). The OAA formed by the GOT according to equation (1a) is hereby reacted simultaneously with the α-KG present in the test with dinitrophenylhydrazine to give the corresponding coloured hydrazone which, after alkalisation, can be determined at 550 nm. The calculation is complicated but possible because the hydrazone of α-ketoglutarate, and the hydrazone of OAA, each have different extinctions in the measurement range.

Furthermore, the OAA formed according to equation (1a) can also be coupled with diazonium salts to give a dyestuff which can be evaluated photometrically. Such a process is described by A. L. Babson (Clin. Chem., 6, 394/1960). The GOT activity can be measured herewith. The amount of the azo dyestuff formed can be measured in visible light.

Furthermore, Federal Republic of Germany Pat. No. 29 11 481 describes the detection of GOT via OAA, starting from equation (1a), in the following reaction chain:

(3a)

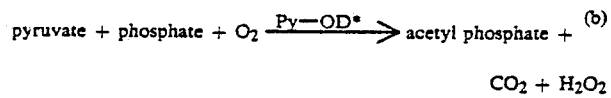

(b)

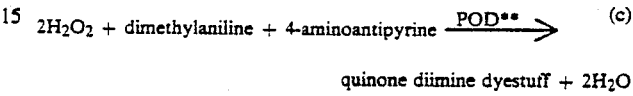

(c)

*Py—OD = pyruvate oxidase
**POD = peroxidase

The extinction increase of the dyestuff formed is measured at 525 to 600 nm.

Federal Republic of Germany Pat. No. 28 34 706 describes a GOT colour test which measures the α-KG formed in the reverse reaction of equation (1a in the following reaction chain:

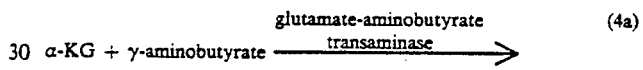

(4a)

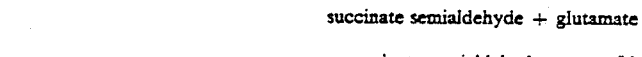

(b)

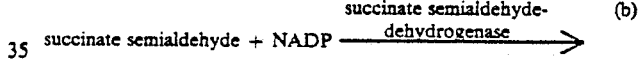

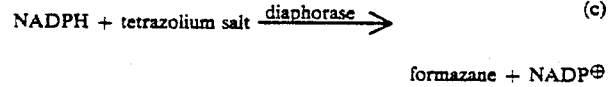

(c)

The formazane formed is measured at an appropriate wavelength.

U. Lippi and G. Guidi (Klin. chem. Akta, 28, 431-437/1970) measured GOT with the help of the glutamate liberated in equation (1a) in which the following two indicator reactions follow:

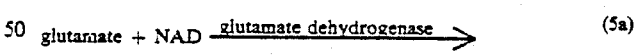

(5a)

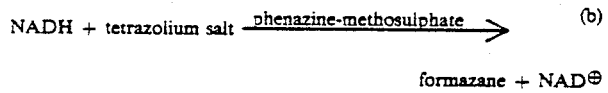

(b)

R. B. Domecq, M. Carta and E. F. de Armorky (Biochem. Klinika, 2, 25-36/1971) combined, for the determination of GOT, the reaction sequence of equations (1a), (2) and (5b).

In this determination, the decrease in the amount of NADH is measured.

It can be monitored in visible light and is also a measure for the activity of GOT in the sample.

For the measurement of the pyruvate formed according to (1b) from alanine sulphinic acid, there is described, for example, in Federal Republic of Germany Pat. No. 30 26 854, the detection with NADH and LDH according to the following equation:

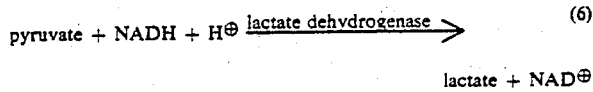
(6)

The decrease of the NADH, measured at 365 nm, is the measurement signal.

All the above-described test processes for the determination of GOT activity suffer from various serious deficiencies, which make their use expensive or difficult. Thus, the processes according to A. Karmen or according to Federal Republic of Germany Pat. No. 30 26 854 admittedly permit the measurement of the extinction change per minute of NADH, which is advantageous, but a UV test must be used. However, as is known to the expert, optical measurement devices for measurement in UV light are especially laborious and, therefore, more expensive than measurement arrangements which can measure the absorption changes in visible light. A further serious deficiency is the fact that a decrease of the NADH extinction must be measured. In such a test, for measurement-technical reasons, only a limited concentration of NADH can be present. The result of this is that the indicator enzymes MDH or LDH used are not saturated with their substrate NADH and, consequently, do not achieve the maximum reaction velocity. This must be compensated for by increasing the enzyme use. This is not only uneconomical but also includes the danger that other interfering enzyme activities are entrained in comparatively large amounts into the test system. A further disadvantage of the low NADH concentration follows from the fact that not only in automatic analysers but also in the case of a manual test, a certain period of time elapses between the addition of the sample and the commencement of the measurement. If a large activity of GOT is present in the sample, then a large amount of the NADH is consumed before commencement of the measurement. Therefore, precisely in the case of greatly increased GOT values, which provide indications of a pathological condition in the body, there is measured too low an activity or no activity at all. This is a serious disadvantage of the determinations.

In the case of the methods according to Reitmann and Frankel, the hydrazones formed are determined in visible light. This makes possible the use of simpler and thus less expensive photometric devices. However, the method is very insensitive and requires the very long incubation time of 1 hour. Only then has sufficient OAA formed so that the hydrazone formation can be initiated. This requires a further incubation time. Furthermore, the α-KG also necessary in the test reacts to give a coloured hydrazone. Extremely complicated relationships are thereby given for the evaluation of the test since, at the same time, the decrease of α-KG hydrazone and the increase of OAA hydrazone must be taken into account. Therefore, it has long been known to the expert that, in the case of these methods, errors of 20 to 30% must be taken into account. Fundamentally similar problems arise in the case of Babson's method. Admittedly it is here also possible to measure in visible light and, because α-KG does not interfere with the diazonium salt, the evaluation is substantially simpler but here, too, OAA must first be produced by a comparatively long incubation. Subsequently, the colour formation must be carried out in a further incubation step.

Furthermore, it is known to the expert that many substances present in the solutions to be investigated also couple with the diazonium salt to give dyestuffs which interfere with the determination because they simulate too high values. These errors must first be eliminated by a blank. Thus, for example, serum always contains varying amounts of acetoacetic acid which simulates oxalacetate which is first to be formed by the GOT reaction.

In the case of the process according to Federal Republic of Germany Pat. No. 29 11 481, it is disadvantageous that, in all, four different enzymatic reactions must be coupled. This leads, in any case, to a comparatively long lag phase until, in the whole chain, all the enzymes have reached substrate saturation. Furthermore, the danger of entraining interfering foreign and side activities into the test is the greater, the more enzymes participate in the reaction chain. Furthermore, the cost per test increases with each enzyme used. On the other hand, this test can be used favorably to kinetically monitor an increase in dyestuff formation.

The same disadvantages of the multiple coupled test are also present in the case of the GOT test according to Federal Republic of Germany Pat. No. 28 34 706, whereby here the measurement with OAA as substrate is also to be added. OAA, being β-ketocarboxylic acid, is very unstable and tends towards decarboxylation.

The method according to Lippi and Guidi also measures in the visible range. It requires only one incubation step but, since this takes 55 minutes, it is also very long. The reaction must be stopped with hydrochloric acid, which is unpleasant to handle. A further disadvantage is that relatively large amounts of glutamic acid are present in serum. According to equation (5a), they simulate GOT in the test. Therefore, here, too, a blank must be used.

The process of Domecq et al. again requires two incubation steps. Since it finally measures the decrease of NADH, corresponding to the method of Karmen, the same disadvantages occur. They appear even more strongly because, for measurement-technical reasons, even less NADH can be used. The measurement in visible light is advantageous. Here, too, the complete consumption of NADH by too high an activity of GOT can falsify the measurement. In all, however, as is readily apparent to the expert, the process is very laborious and subject to error since it necessitates the highest requirements for the precise dosing of NADH in each measurement value.

Thus, it is the object of the present invention to provide a GOT colour test which uses the shortest possible reaction chain and thus a short reaction time, which permits the measurement of the reaction product in visible light and is not disturbed by side reactions of the enzymes or substrates.

Attempts to couple the reaction described in equation (1b) with the reactions described in equations (3b) and (3c) and thus to avoid an enzymatic reaction (3a) and to obtain a reaction product measurable in visible light were unsuccessful. No colour formation is found, even in the case of the highest GOT activities. Also in the case of replacement of the dimethylaniline by other anilines or phenols, which are known as coupling components for the so-called PAP systems, no reaction is obtained, even when 4-aminoantipyrine is replaced by other couplable, nucleophilic reagents, such as 3-methyl-benzthiazolone-2-hydrazone or its 6-sulphonyl compound. However, the whole substance class of the heteroaromatic azines which give intensely coloured radicals with POD/$H_2O_2$ or o-toluidine or tetramethyl-benzidine, which also form deep coloured radicals, give no reaction in the test. The cause for this could be shown to be that not only alanine-sulphinic acid, which serves as substrate for GOT and, therefore, must be used in large amounts in the test, but also the sulphite formed in the GOT reaction, due to its strong reduction action and due to its ability itself to enter into oxidative couplings, suppress the colour formation. Surprisingly, however, we have found certain substrates with which equation (3c) is not disturbed either by sulphur dioxide or by alanine-sulphinic acid. Such compounds include, for example, N-(3'-sulphonyl-4'-hydroxy-5'-chlorophenyl)-4-aminoantipyrine (SHYC-AA) and 4,5-bis-[4-dimethylaminophenyl]-2-[3,5-dimethoxy-4-hydroxyphenyl]-imidazole (B-DDH-imidazole).

Thus, according to the present invention, there is provided a process for the determination of the activity of glutamate-oxalacetate-transaminase (GOT) in aqueous solutions in which (a) α-ketoglutarate is reacted with alanine-sulphinic acid, catalysed by GOT, to give pyruvate, sulphur dioxide and glutamate, (b) the resultant pyruvate is reacted with phosphate and oxygen, catalysed by pyruvate oxidase, to give acetyl phosphate, carbon dioxide and hydrogen peroxide, (c) the hydrogen peroxide and a chromogen is reacted, catalysed by a peroxidase, to give a dyestuff and water and (d) the amount of dyestuff formed is determined, wherein the chromogen used is N-(3'-sulphonyl-4'-hydroxy-5'-chlorophenyl)-4-aminoantipyrine (SHYC-AA), 4,5-bis-[4-dimethylaminophenyl-]2-[3,5-dimethoxy-4-hydroxyphenyl]-imidazole (B-DDH-imidazole) or a related substance.

The process according to the present invention can be carried out in the presence of a water-soluble magnesium salt, thiamine pyrophosphate, flavine-adenine-dinucleotide and/or a buffer of pH 6-7.

It is very surprising that some special compounds permit an undisturbed measurement of the activity of GOT to be carried out. It is especially surprising in the case of SHYC-AA since the fundamental reaction between 2,4-dichlorophenyl-6-sulphonic acid and 4-aminoantipyrine, which give the same dyestuff by oxidative coupling, is, like all PAP reactions, completely suppressed by alanine-sulphinic acid and sulphite.

The process can be carried out in a cuvette, the amount of dyestuff formed being measured by light transmission or it can be carried out on a carrier impregnated with the reagents, the dyestuff formed being determined by remission.

Furthermore, the present invention provides an analytical agent for the detection of GOT, said agent comprising α-ketoglutarate, alanine-sulphinic acid, a chromogen, peroxidase, pyruvate oxidase, soluble phosphate, buffer ahd water, wherein the chromogen is N-(3'-sulphonyl-4'-hydroxy-5'-chlorophenyl)-4-aminoantipyrine (SHYC-AA) or 4,5-bis-[4-dimethylaminophenyl]-2-[3,5-dimethoxy-4-hydroxyphenyl]-imidazole (B-DDH-imidazole).

An advantageous analytical agent according to the present invention consists of a mixture of the reagents with the following composition:

(a) 1 mmol α-ketoglutarate
  1-20 mmol alanine-sulphinic acid
  0.05-10 mmol chromogen
  100-10,000 U peroxidase
  50-20,000 U pyruvate oxidase
  0.5-5 mmol soluble phosphate
  1-100 mmol buffer (pH 6-7).

10-1000 ml. of water are added for the production of the reagent solution which, depending upon the size of the test batches and upon the concentration of the investigated solutions, can be used for about 100-1000 tests.

For the activation of the enzymes, the reagent mixture preferably also contains (b) 0.5-5 mmol of a water-soluble magnesium salt
  0.05-1 mmol thiamine pyrophosphate and/or
  0.01-0.1 mmol flavine-adenine-dinucleotide (FAD).

The reagents can be present in the form of a mixture ready for use or in the form of a lyophilisate or can be impregnated into test strips or can also be divided up into amounts coordinated with one another in containers assembled to give a commercial packing or can be present in one or more tablets which may have several layers with differing composition which are only combined for the reaction by mixing with an appropriate solvent, for example a buffer solution or a test fluid, to give the reagent mixture ready for use.

The following Examples are given for the purpose of illustrating the present invention:

EXAMPLE 1

Measurement of GOT in a Photometer

To 1 ml. of the following solution 40 mmol 4-(2-hydroxyethyl)-1-piperazine-ethane-sulphonic acid (HEPES)/potassium hydroxide, pH 6.7

200 mmol alanine-sulphinic acid
0.5 mmol potassium dihydrogen phosphate
10 mmol magnesium chloride
0.5 mmol thiamine pyrophosphate
0.01 mmol ethylenediamine-tetraacetic acid
0.1 mmol N-(3'-sulphonyl-4'-hydroxy-5'-chlorophenyl)-4-aminoantipyrine
12 mmol α-ketoglutarate
1000 U peroxidase
2500 U pyruvate oxidase
ad 1000 ml. water are added 0.02 ml. human serum. Commencement of measurement after 2 minutes, T=25° C., λ=546 nm, ε=19.6 $cm^2$ μmol. Measurement value is the εE/min up to 5 minutes after commencement of measurement. The measurement can be carried out between 450 and 580 nm. but the ε must be determined in each case for the desired wavelengths.

EXAMPLE 2

GOT In Test Strips

For the production of test strips, 2 papers are impregnated:

A. ENZYME PAPER 0.5 mol/l. morpholinoethane-sulphonic acid (MES)/potassium hydroxide, pH 6.5
200 mmol/l. alanine-sulphinic acid
1 mmol/l. potassium dihydrogen phosphate
10 mmol/l. magnesium chloride
0.5 mmol/l. thiamine pyrophosphate
0.01 mmol/l. FAD
20,000 U/l. POD
250,000 U/l. Py-OD With this solution, an absorbent paper is impregnated (thickness 50 μm., weight per unit area 12 g./m², absorbency 50 g. H₂O/ m²) and dried for 5 minutes at 30° C.

The paper is subsequently cut up into strips of 1 cm. breadth.

B. INDICATOR PAPER 10 mmol/l. 4,5-bis-[4-dimethylaminophenyl]-2-[3,5-dimethoxy-4-hydroxyphenyl]-imidazole (B-DDH-imidazole)
18 mmol/l. α-KG
0.1 mmol/l. Hcl as solvent.

With this solution, an appropriate absorbent paper is also impregnated, dried for 5 minutes at 30° C. and cut up into strips of 1 cm. breadth. The material is worked up in an especially advantageous manner to give test strips corresponding to FIG. 1 of the accompanying drawings. A 1 cm. wide, transparent polycarbonate film (3) of 100 μm. thickness is thereby fixed, together with the indicator paper and the enzyme paper (4) corresponding to FIG. 1, on one side of a plastics strip so that the film (3) is on the outside, the indicator paper in the middle and the enzyme paper on the inside. Next thereto, a 15 mm. wide glass fibre fleece (2) (thickness 1.5 mm., fibre thickness about 2 μm.) is applied so that the free end of the film and the impregnated papers still extend 6 mm. over the fleece. It is then cut up into 6 mm. wide test strips. When 15 μl. of whole blood are applied to the sample application zone (2a) according to FIG. 1, then, within 30 to 60 seconds, the plasma component penetrates the whole of the glass fibre fleece even below the transparent film, whereas the erythrocytes are held in the zone (2a). By pressing on the film, the enzyme and the indicator paper (4) now come into contact with the separated plasma and are uniformly moistened through. The GOT contained in the plasma reacts with a blue coloration, the intensity of which is proportional to the amount of GOT and can possibly be measured in a remission photometer. Other sample materials, such as serum or plasma, also react in the same way.

It will be understood that the specification and examples are illustrative but not limitative of the present invention and that other embodiments within the spirit and scope of the invention will suggest themselves to those skilled in the art.

What is claimed is:

1. A process for the determination of the activity of glutamate-oxalacetate-transaminase (GOT) in an aqueous solution sample comprising
    (a) reacting alpha-ketoglutarate with alanine-sulphinic acid, catalysed by GOT, to give pyruvate, sulphur dioxide and glutamate,
    (b) reacting the resultant pyruvate with phosphate and oxygen, catalyzed by pyruvate oxidase, to give acetyl phosphate, carbon dioxide and hydrogen peroxide,
    (c) reacting the hydrogen peroxide formed, and a chromogen selected from the group consisting of N-(3'-sulphonyl-4'-hydroxy-5'-chlorophenyl)-4-aminoantipyrine (SHYC-AA) and 4,5-bis-[4-dimethylaminophenyl]-2-[3,5-dimethoxy-4-hydroxyphenyl]-imidazole (B-DDH-imidazole), catalysed by a peroxidase, to give a dyestuff and water and
    (d) determining the amount of dyestuff formed as a measure of the activity of GOT in the sample.

2. The process of claim 1, wherein the reactions are carried out in the presence of a water-soluble magnesium salt, thiamine pyrophosphate, flavine-adenine dinucleotide and/or buffer of pH 6-7.

3. The process of claim 1 wherein the reaction is carried out in a cuvette, the amount of the dyestuff formed being measured by light transmission.

4. The process of claim 3, wherein the reagents are in the dry form of a lyophilisate, a tablet or impregnated carrier and are prepared for the process by dissolving the reagent in the required amount of water, buffer solution or sample liquid.

5. The process of claim 1 wherein the reaction takes on an absorbent carrier impregnated with the reagents with the application of the sample; and determining the dyestuff formed is accomplished by remission photometry.

6. The process of claim 2 wherein the reaction takes place on an absorbent carrier impregnated with the reagents with the application of the sample; and determining the dyestuff formed is accomplished by remission photometry.

7. Analytical agent for the determination of the activity of GOT, comprising alpha-ketoglutarate, alanine-sulphinic acid, a chromogen, peroxidase, pyruvate oxidase, soluble phosphate, buffer and water, wherein the chromogen is N-(3'-sulphonyl-4'-hydroxy-5'-chlorophenyl)-4-aminoantipyrine (SHYC-AA) or 4,5-bis-[4-dimethylaminophenyl]-2-[3,5-dimethyoxy-4-hydroxyphenyl]-imidazole (B-DDH-imidazole).

8. Analytical agent according to claim 7, wherein there is additionally present a soluble magnesium salt, thiamine pyrophosphate and flavine-adenine-dinucleotide (FAD).

9. Analytical agent according to claim 7, containing for each 1 mmol alpha-ketaglutarate: 1-20 mmol alanine-sulphinic acid, 0.05-10 mmol chromogen, 100-10,000 U peroxidase, 50-20,000 U pyruvate oxidase, 0,5-5 mmol soluble phosphate, 1-100 mmol buffer (pH 6-7) and 10-1000 ml. water, wherein the chromogen is N-(3'-sulphonyl-4'-hydroxy-5'-chlorophenyl)-4-aminoantipyrine (SHYC-AA) or 4,5-bis-[4-dimethylaminophenyl]-2-[3,5-dimethyoxy-4-hydroxyphenyl]-imidazole (B-DDH-imidazole).

10. Analytical agent according to claim 9, wherein there additionally present 0.5 to 5 mmol of a water-soluble magnesium salt, 0.05-1 mmol thiamine-pyrophosphate and/or 0.01-0.1 mmol flavine-adenine-dinucleotide (FAD).

11. Analytical agent according to claim 7, containing 40 mmol HEPES/KOH (pH 6.7), 200 mmol alanine-sulphinic acid, 0.5 mmol potassium dihydrogen phosphate, 10 mmol magnesium chloride, 0.5 mmol thiamine pyrophosphate, 0.01 mmol flavine-adenine-dinucleotide, 0.5 mmol ehtylenediamine-tetraacetic acid, 0.1 mmol N-(3'-sulphonyl-4'-hydroxy-5'-chlorophenyl)-4-aminoantipyrine, 12 mmol alpha-ketoglutarate, 1000 U peroxidase, 2500 U pyruvate oxidase and 1000 ml. water.

12. Analytical agent according to claim 7, comprising
    (a) a first paper which has been impregnated with a solution of 0.5 mmol/l.MES/KOH (pH 6.5), 200 mmol/l. alanine-sulphinic acid, 1 mmol/l.KH₂PO₄, 10 mmol/l. MgCl₂, 0,5 mmol/l. thiamine pyrophosphate 0,01 mmol/l. FAD, 20,000 U/l. POD and 250,000 U/l. Py-OD and
    (b) a second paper which has been impregnated with a solution of 10 mmol/l. B-DDH-imidaz 18 mmol/l. alpha-KG and 0.1 mmol/l. HCl as solvent, said first and second papers being secured together on a carrier foil.

* * * * *

UNITED STATES PATENT AND TRADEMARK OFFICE
CERTIFICATE OF CORRECTION

PATENT NO. : 4,591,553

DATED : May 27, 1986

INVENTOR(S) : Ulfert Deneke et al

It is certified that error appears in the above-identified patent and that said Letters Patent is hereby corrected as shown below:

Col. 1, line 56, delete "hereby".
Col. 2, lines 26-27 should read after "equation"-- 1a), in the following reaction chain: --.
Col. 2, line 62, change "in" first occurrence to -- In --.
Col. 8, line 43, after "there" insert -- is --.
Col. 8, line 64, change "B-DDH-imidaz" to -- B-DDH-imidazole, --.

Signed and Sealed this

Tenth Day of March, 1987

Attest:

DONALD J. QUIGG

Attesting Officer

Commissioner of Patents and Trademarks